US012644083B2

(12) United States Patent
Hughes et al.

(10) Patent No.: US 12,644,083 B2
(45) Date of Patent: Jun. 2, 2026

(54) DUAL CIRCULATION MICROPHYSIOLOGICAL SYSTEM

(71) Applicant: CN Bio Innovations Limited, Thame (GB)

(72) Inventors: David James Hughes, Thame (GB); Tomasz Kostrzewski, Thame (GB)

(73) Assignee: CN BIO INNOVATIONS LIMITED, Cambridgeshire (GB)

( * ) Notice: Subject to any disclaimer, the term of this patent is extended or adjusted under 35 U.S.C. 154(b) by 1228 days.

(21) Appl. No.: 17/440,843

(22) PCT Filed: Mar. 10, 2020

(86) PCT No.: PCT/GB2020/050577
§ 371 (c)(1),
(2) Date: Sep. 20, 2021

(87) PCT Pub. No.: WO2020/188243
PCT Pub. Date: Sep. 24, 2020

(65) Prior Publication Data
US 2022/0162534 A1     May 26, 2022

(30) Foreign Application Priority Data

Mar. 20, 2019    (GB) ...................................... 1903813

(51) Int. Cl.
*C12M 3/06*          (2006.01)
*C12M 1/00*          (2006.01)
(Continued)

(52) U.S. Cl.
CPC ............ *C12M 23/16* (2013.01); *C12M 23/34* (2013.01); *C12M 25/14* (2013.01); *C12M 29/14* (2013.01);
(Continued)

(58) Field of Classification Search
CPC ...... C12M 23/16; C12M 23/34; C12M 25/14; C12M 29/18; C12M 41/44; C12N 5/0671
(Continued)

(56) References Cited

U.S. PATENT DOCUMENTS 6,197,575 B1    3/2001  Griffith et al.
9,260,688 B2 *  2/2016  Hung ..................... C12M 41/46
(Continued)

FOREIGN PATENT DOCUMENTS

CN        104822821        8/2015
CN        106232801        12/2016
(Continued)

OTHER PUBLICATIONS

Rathbone et al., "A low volume oxygenator for open well liver on a chip tissue culture". (Year: 2018).*
(Continued)

*Primary Examiner* — Michael L Hobbs
*Assistant Examiner* — Lenora A Abel
(74) *Attorney, Agent, or Firm* — Woods Oviatt Gilman LLP; Katherine H. McGuire, Esq.

(57) ABSTRACT

A microfluidic cell culture system is provided. The system includes a dual circulation arrangement for providing the cell culture with culture medium (and, optionally, selected compounds for study). The dual circulation arrangement permits culture conditions to be readily modified for different phases of cell culture. In particular, a first circulation route can be used to circulate a relatively high volume of medium, thereby allowing a low cell number to medium volume ratio, and a second circulation route can be used to circulate a relatively low volume of medium, thereby allowing a high cell number to medium volume ratio. The first circulation is optimised for a pre-culture period, before test compounds are added, and the second circulation is opti- (Continued)

mised for the test phase, providing a high cell number to medium ratio while preserving function during the test period.

14 Claims, 2 Drawing Sheets

(51) Int. Cl.
|  |  |
|---|---|
| *C12M 1/12* | (2006.01) |
| *C12M 1/34* | (2006.01) |
| *C12N 5/071* | (2010.01) |

(52) U.S. Cl.
CPC ............ *C12M 29/18* (2013.01); *C12M 41/44* (2013.01); *C12N 5/0671* (2013.01); *C12N 2513/00* (2013.01)

(58) Field of Classification Search
USPC ...................................................... 435/289.1
See application file for complete search history.

(56) References Cited

U.S. PATENT DOCUMENTS

| | | | | |
|---|---|---|---|---|
| 2003/0215941 | A1* | 11/2003 | Campbell | .............. C12M 25/02 |
| | | | | 435/325 |
| 2005/0260745 | A1 | 11/2005 | Domansky et al. | |
| 2008/0145922 | A1 | 6/2008 | Lehmann et al. | |
| 2016/0377599 | A1 | 12/2016 | Hughes et al. | |

FOREIGN PATENT DOCUMENTS

| | | | | |
|---|---|---|---|---|
| CN | 107949635 | 4/2018 | | |
| CN | 109152797 | 1/2019 | | |
| EP | 2322913 | 10/2012 | | |
| JP | 2005514058 | 5/2005 | | |
| WO | 2013175580 | 11/2013 | | |
| WO | WO-2013175580 A1 | * 11/2013 | ........... | C12M 29/10 |
| WO | 2016158233 | 10/2016 | | |
| WO | 2017/164797 | 9/2017 | | |
| WO | 2017154880 | 9/2017 | | |
| WO | 2017/176357 | 10/2017 | | |
| WO | WO 2018/037402 | 3/2018 | | |

OTHER PUBLICATIONS

WO-2013175580-A1 (Year: 2013).*
Rathbone, Daniel R.; "A Low Volume Oxygenator for Open Well Liver-on-a-Chip Tissue Culture"; Submitted to the Department of Mechanical Engineering in partial fulfillment of the requirements for the degree of Master of Science in Mechanical Engineering at the Massachusetts Institute of Technology, Feb. 2018.
Chan, Tom S., et al.; "Meeting the challenge of predicting hepatic clearance of compounds slowly metabolized by cytochrome P450 using a novel hepatocyte model, HepatoPac"; Drug Metabolism and Disposition, vol. 41, No. 12; DMD 41:2024-2032, 2013.
Di, Li, et al.; "A novel relay method for determining low-clearance values"; Drug Metabolism and Disposition, vol. 40, No. 9; DMD 40:1860-1865, 2012.
Mvares, Aurelie, et al.; "Morphological behaviour and metabolic capacity of cryopreserved human primary hepatocytes cultivated in a perfused multiwell device"; Xenobiotica, 45(1), pp. 29-44, 2015.
Rowe, Cliff, et al.; "Perfused human hepatocyte microtissues identify reactive metabolite-forming and mitochondria-perturbing hepatotoxins"; Toxicology in Vitro 46, pp. 29-38, 2018.

* cited by examiner

PRE-CULTURE PERIOD

---- = liquid level

TEST PERIOD (WITH DRUG)

---- = liquid level

EMBODIMENT FOR TRANSWELL WITH GUT CELLS

DUAL CIRCULATION
MICROPHYSIOLOGICAL SYSTEM

FIELD OF THE INVENTION

The present invention relates to a microphysiological system for cell culture, primarily for the purpose of providing means to study drug metabolism. The microphysiological system may also be termed a microfluidic cell culture system or organ-on-a-chip. The system includes a dual circulation arrangement for providing the cell culture with culture medium (and, optionally, selected compounds for study). The dual circulation arrangement permits culture conditions to be readily modified for different phases of cell culture. Aspects of the invention further relate to methods of cell culture, and of studying drug metabolism.

BACKGROUND TO THE INVENTION

Drug metabolism is the conversion of a parent compound into metabolites which are then typically excreted from the body. The primary organ of drug metabolism is the liver. The measurement of drug metabolism in vitro is an essential part of the drug development process. To achieve accurate measurements two fundamental requirements are: i) an in vitro system with the functional capacity to metabolise the test compound/drug, ii) a sufficiently high cell number to medium volume ratio to ensure the concentration of parent and/or metabolite can be accurately measured. This measurement is typically undertaken using liquid chromatography.

Current technologies used for drug metabolism include microsomes, suspension hepatocytes, and plated hepatocytes. All of these technologies have the significant disadvantage that the functional performance of the microsomes/cells in the system decreases, in some cases very rapidly, with time. This makes them unsuitable for measurement of slowly metabolised compounds as the compound must be left in contact with the measurement system for extended periods. During this extended periods cells stop functioning and/or die. For example in suspension culture, hepatocytes can not be maintained for more than 6 hours. A solution to this problem was proposed by Di et al (Di L, Trapa P, Obach R S, Atkinson K, Bi Y A, Wolford A C, Tan B, McDonald T S, Lai Y, Tremaine L M., A novel relay method for determining low-clearance values, Drug Metab Dispos. 2012 September; 40(9):1860-5), in which compound is incubated for short periods with suspension cells and then transferred to a fresh culture, known as the relay method. While successful the process is time consuming and requires large numbers of cells. In an alternative solution, Chan et al (Chan T S, Yu H, Moore A, Khetani S R, Tweedie D. Meeting the challenge of predicting hepatic clearance of compounds slowly metabolized by cytochrome P450 using a novel hepatocyte model, HepatoPac. Drug Metab Dispos. 2013 December; 41(12):2024-32) incubated compounds with a co-culture of hepatocytes and mouse fibroblasts (Hepatopac) for a period of 7 days to allow sufficient time for measurable disappearance of parent compound or production of metabolites. Again this results in a long and labour intensive assay.

Microphysiological systems (or organ-on-chip) are highly functional in vitro cell culture systems which are suitable for drug metabolism experiments. Typically cells are placed in the system and pre-cultured for a number of days, to allow formation of functional microtissues before experimentation with drugs commences, ie the test phase. The culture conditions for this pre-incubation period demand a low cell number to medium volume ratio to remove the need for frequent medium exchanges. This low cell number to medium volume ratio makes accurate determination of the metabolism of slowly metabolised compounds and the detection of rare metabolites challenging.

Example microphysiological systems for the culture of liver cells include those described in U.S. Pat. No. 6,197,575 and US 2005/0260745. These publications disclose systems for culture of liver cells including a single culture medium circulation. PCT/US2017/016721 (published as WO 2017/176357) discloses a cell culture platform in which discrete microphysiological systems are linked to other organs by spillway features. EP 2 322 913 describes an apparatus for analysis of cells disposed in media in multiple wells of a multi-well plate, including barriers for insertion into wells of the multi-well plate. US 2008/145922 describes a device for detection of metabolic activity of cells in culture, which includes a movable separation element to border a reaction space.

It is among the objects of embodiments of the present invention to provide an alternative microphysiological cell culture system. In preferred embodiments, the system is intended to permit drug metabolism experiments to be conducted more easily; in particular, experiments with slowly metabolised compounds, or with rare metabolites, will be enabled with the present invention. Other objects and advantages will be apparent from the description.

SUMMARY OF THE INVENTION

The present invention addresses the disadvantages of the prior art by providing a microphysiological cell culture system which includes two separate culture medium circulation routes. The first route can be used to circulate a relatively high volume of medium, thereby allowing a low cell number to medium volume ratio, and the second route can be used to circulate a relatively low volume of medium, thereby allowing a high cell number to medium volume ratio. The first route can be used in the pre-culture phase of growth, and then the second route switched to when a metabolite assay is to be carried out. The first circulation is optimised for the pre-culture period, before compounds are added, and the second circulation is optimised for the test phase, providing a high cell to medium ratio while preserving function during the test period. Microphysiological systems enable cells to be kept in culture for extended periods of many weeks, overcoming the limitations inherent in the culture of cells in suspension, where liver cells die within 6 hours.

According to a first aspect of the present invention, there is provided a microphysiological cell culture system, the system comprising:

a cell culture chamber;

first and second fluidic circuits, each connected to said chamber at a chamber outlet and a chamber inlet, wherein at least the first and second circuit chamber outlets are at separate positions;

wherein the cell culture chamber defines a first fluid fill level and a second fluid fill level, the first fluid fill level representing a greater volume of fluid than the second fluid fill level; and wherein the first fluidic circuit chamber outlet is positioned at the first fluid fill level or between the first and second fluid fill levels, and the second fluidic circuit chamber outlet is positioned at or below the second fluid fill level; such that either the first or both first and second fluidic circuits are able to operate when the chamber is filled with fluid to the first fill level, and only the second fluidic circuit is able to operate when the chamber is filled with fluid to the second fill level.

Thus, the system can be filled with medium to the first fill level for an initial pre-culture period. This first fill level allows both first and second fluidic circuits to operate, so providing circulation of a relatively large volume of culture medium. Once the cell culture is established, the medium may be replaced with a smaller volume of medium, to the second fill level, and the test compound added.

The system may comprise means for switching between operation of the first and the second fluidic circuits. For example, each circuit may include a separately operable micropump or similar, which may be switched on or off as required. The system may further comprise a controller for operating the micropumps. In certain embodiments, either or both of the first and second fluid circuits may comprise a valve to permit closure of the circuit. Again, the system may comprise a controller for operating the valves. Although not essential to include one or more valves, it is highly preferred to provide at least a valve which closes off the first circuit during the test phase so as to ensure medium does not pass into this circuit during the test. Medium passing into the first circuit during the test phase has the potential to reduce the accuracy of the test as the volume in the second circuit will change, hence rates of concentration change will be altered.

The cell culture chamber may define a location for receiving cells, said location being positioned at or below the second fluid fill level. Given that the second fill level represents a relatively small volume, this positioning permits the cells to be placed just below the second fill level so allowing sufficient oxygen to reach the culture during the test phase.

In certain embodiments, the first and second fill levels are defined by walls of the cell culture chamber of first and second heights, said walls defining the first and second chamber outlets. Other barriers may be used. The system may comprise a further wall enclosing both first and second walls of the cell culture chamber. This arrangement permits a simple way of defining the chamber outlets in the form of a spillway leading from and defined by the first and/or second walls. Use of a spillway also has the advantage that it provides a simple way for one or both of the fluid circuits to include a portion which is exposed to the environment, permitting re-oxygenation of circulating medium (particularly important when the system is filled to the first fill level, and the cells may not be adjacent the fill level so restricting access to dissolved oxygen). The spillways may lead into culture medium reservoirs included in the fluid circuits, from which medium may be returned to the culture chamber.

The first fluidic circuit typically has a greater volume than that of the second fluidic circuit—for example, at least 2, 3, 5, 10 or more times greater. While not essential, given that use of both first and second circuits will inherently permit circulation of a greater volume of medium than only the second circuit, use of differentially-sized circuits allows the volume differential to be significantly greater. In certain embodiments, typical volumes may be 1000-5000 μL for the first circuit, preferably 1500-4000 μL, more preferably 1500-3000 μL, and most preferably around 2000 μL. In preferred embodiments the volume of the second circuit is around one tenth of that of the first; typical volumes may be 100-500 μL for the first circuit, preferably 150-400 μL, more preferably 150-300 μL, and most preferably around 200 μL. The first fluidic circuit is preferably longer than the second, more preferably at least 2, 3, 5, 10 times longer. In most preferred embodiments, the first fluidic circuit is significantly longer than the second, and in particular the spillway portions of the first circuit are at least 25, 50, or 100 times longer than the spillway portions of the second circuit. For example, in a specific embodiment, it may be that the first circuit would have a spillway of 10 cm and the second circuit a spillway of 1 mm.

Preferably either or both of the first and second fluidic circuits comprises at least a portion which is exposed to the environment; more preferably at least the first circuit does so.

The system may further comprise at least one reservoir which is not part of the fluidic circuits for receiving a liquid; preferably the at least one reservoir is adjacent the second fluidic circuit. Additional reservoirs may be provided, for example, adjacent the first fluidic circuit. The reservoirs in use may be filled with liquid; this may help to increase local humidity and reduce evaporation from the system, which can be a particular concern with small volumes of circulating medium.

In embodiments, the chamber may comprise a cell culture; for example, a hepatocyte cell culture; or a lung, gut, or kidney cell culture. The cell culture may be comprised within a 3D scaffold or a TRANSWELL® insert. The skilled person will be aware of means for generating 3D scaffold or TRANSWELL® inserts for cell culture.

An aspect of the invention provides a method for culturing cells, the method comprising:

placing cells to be cultured in a system as defined herein;

placing culture medium in the system to the first fluid fill level;

operating the first fluid circuit and optionally also the second fluid circuit to circulate said culture medium, and culturing said cells;

removing or replacing culture medium in the system to the second fluid fill level; and operating only said second fluid circuit to circulate said culture medium, and culturing said cells.

Preferably both the first and second fluid circuits are operated together when the culture medium is at the first fill level. When operation switches to the second fluid circuit only, this is preferably operated at the combined rate of first and second circuits (or the rate of the first circuit only, where the second was not operated at the first fill level). This maintains the same overall medium flow in the first and second stages of cell culture of the method, so reducing variability.

The invention further provides a method for investigating drug metabolism in a cell culture, the method comprising:

placing cells to be cultured in a system as defined herein;

placing culture medium in the system to the first fluid fill level;

operating the first fluid circuit and optionally also the second fluid circuit to circulate said culture medium, and culturing said cells;

removing or replacing culture medium in the system to the second fluid fill level, said culture medium comprising a drug whose metabolism is to be investigated;

operating only said second fluid circuit to circulate said culture medium, and culturing said cells; and analysing said culture medium to determine presence or absence of drug metabolites.

The culture medium may be analysed by any suitable means; for example, liquid chromatography of the medium.

BRIEF DESCRIPTION OF THE DRAWINGS

These and other aspects of the invention will now be described by way of example only and with reference to the accompanying drawings, in which.

DETAILED DESCRIPTION OF THE INVENTION

Figure 1:
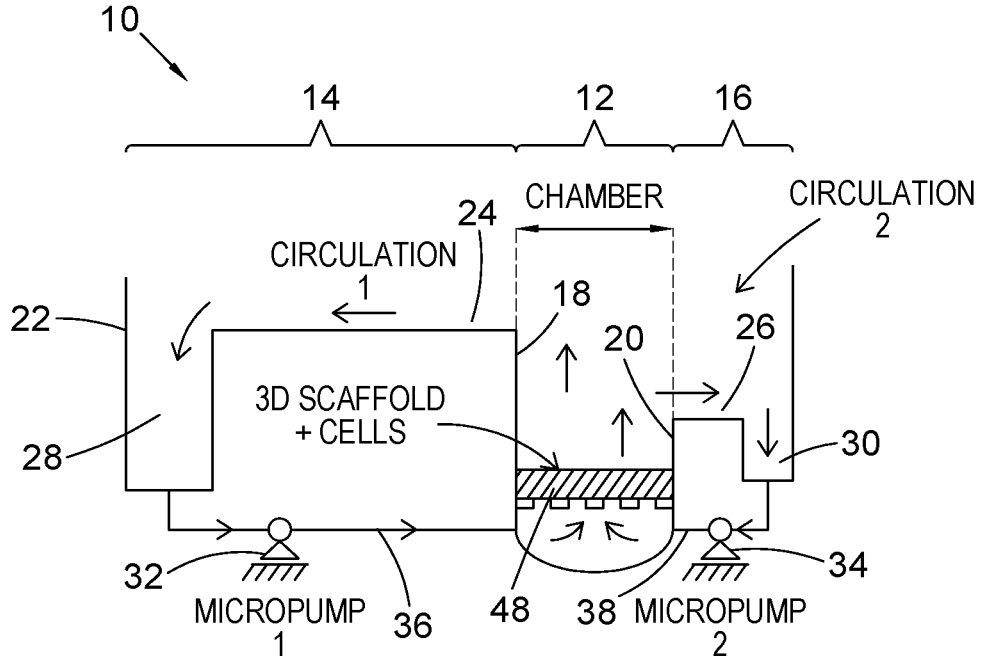
FIG. 1 shows a schematic side sectional view of a microphysiological cell culture system according to an embodiment of the invention.
Figure 2:
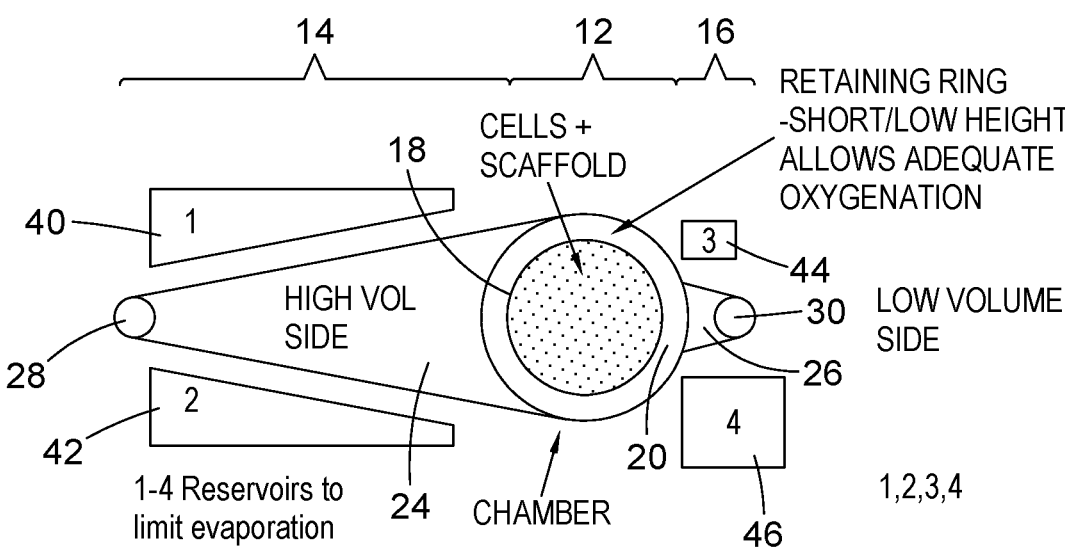
FIG. 2 shows a schematic top view of the system of FIG. 1.

A microphysiological cell culture system according to an embodiment of the invention is shown in schematic side sectional view in FIG. 1, and in schematic top view in FIG. 2. Referring to both Figures, the cell culture system 10 includes a cell culture chamber 12, and first 14 and second 16 fluid circuits. The cell culture chamber 12 is bounded by first and second walls 18, 20 of differing heights. The system as a whole is bounded by a further wall 22. The first wall 18 defines (by its height) a first fluid fill level (see 52 in FIG. 3), and likewise the second wall 20 defines a second fluid fill level (see 54 in FIG. 4). The first fluid fill level represents a greater volume than the second fluid fill level.

Each wall further defines a first and second outlet from the chamber 12 in the form of an open spillway 24, 26; fluid above the level of the respective wall 18, 20 will flow along the spillway 24, 26 to a medium reservoir 28, 30. A micropump 32, 34 in each fluid circuit pumps medium from the reservoir 28, 30 through a return channel 36, 38 to return it to the cell culture chamber 12.

As is apparent from the Figures, the first fluid circuit 14 includes the first wall 18, first spillway 24, first medium reservoir 28, first micropump 32, and first return channel 36. The second fluid circuit 16 includes a wall 20, spillway 26, medium reservoir 30, micropump 34, and return channel 38. Further, the first spillway 24 is located at or below the first fluid fill level 52, but above the second fluid fill level 54; while the second spillway 26 is located at or below the second fluid fill level 54. This ensures that when cell culture medium is present in the system at the first fluid fill level 52, both first and second fluid circuits 14, 16 may be operated, while when cell culture medium is present only at the second fluid fill level 54, only the second fluid circuit 16 may be operated.

As shown in FIG. 2, the system also includes a series of reservoirs 40, 42, 44, 46, which are not connected to the fluid circuits. These reservoirs are located adjacent the spillways 24, 26 and medium reservoirs 28, 30.

The cell culture chamber 12 includes a 3D cell scaffold 48 which is seeded with cells, for example, hepatocytes.

In use, the system may be operated as follows.

Liver cells, typically primary human hepatocytes (but other cell types maybe used) are seeded into a 3D scaffold 48 within the culture chamber 12 in the microphysiological system. The design of the scaffold 48 and protocol for the seeding of the cells is known in the art. See, for example, the LiverChip system provided by CN Bio Innovations, and as described in Aurelie Vivares, Sandrine Salle-Lefort, Catherine Arabeyre-Fabre, Robert Ngo, Geraldine Penarier, Michele Bremond, Patricia Moliner, Jean-Francois Gallas, Gerard Fabre & Sylvia Klieber (2015) Morphological behaviour and metabolic capacity of cryopreserved human primary hepatocytes cultivated in a perfused multiwell device, Xenobiotica, 45:1, 29-44, DOI: 10.3109/00498254.2014.944612.

The system is provided with appropriate cell culture medium to the first fill level 52. Both micropumps 32, 34 are operated in order to cause circulation of cell culture medium through the scaffold containing the cells via both first and second fluid circuits 14, 16. After fluid passes through the cell containing scaffold 48 it is returned to the pump 32, 34 via slipways 24, 26, each of which defines a surface channel which allows the fluid to be re-oxygenated through contact with ambient air. Note that the slipway 24 of the first circuit is significantly longer than the slipway 26 of the second circuit (for example, up to 100 times longer); given the greater volume of medium in the first circuit, this assists in reoxygenation of the medium during circulation. This is the first circulation, around which the medium is continuously recirculated. The scaffold typically contains 600 k hepatocytes and the first circulation contains 2000 µL of cell culture medium. This has been proven to maintain highly functional cells and minimise the need to refresh the cell culture medium.

For example, the Vivares et al 2015 paper cited above demonstrates that a 3D liver scaffold (in Vivares et al 2015 arranged as a single loop) maintains liver metabolic function better than primary human hepatocytes cultured in a monolayer. For functional longevity monolayer cultures, which will last a few days are considered superior to suspension cultures, will last a few hours which are widely used for drug metabolism work (e.g. in a relay assay). Further, Rowe et al (Perfused human hepatocyte microtissues identify reactive metabolite-forming and mitochondria-perturbing hepatotoxins, Toxicology in Vitro Volume 46, February 2018, Pages 29-38) demonstrate that a 3D liver scaffold maintains cells for 7 days with a similar metabolic transcriptome as freshly thawed cells. Freshly thawed cells are equivalent to the condition of cells used at the start of a suspension assay, which will then die over the course of the suspension assay.

The second circulation used for the test phase (when compounds are added and metabolism measured) is of a significantly lower volume, circa 200 µL. The second circulation is drawn from the cell culture chamber 12 containing the cell and scaffold at a lower vertical height above the scaffold 48 than the first circulation—see second wall 20 and second spillway 26, along with the second fluid fill level 54. This is important as it allows the second circulation to be operated when the first circulation is empty, and it lessens the volume of cell culture medium above the cell containing 3D scaffold which ensures adequate oxygenation of the cells within the scaffold. The second circulation likewise also contains a micropump 34 which continuously circulates cell culture medium through the cell containing scaffold.

Figure 3:
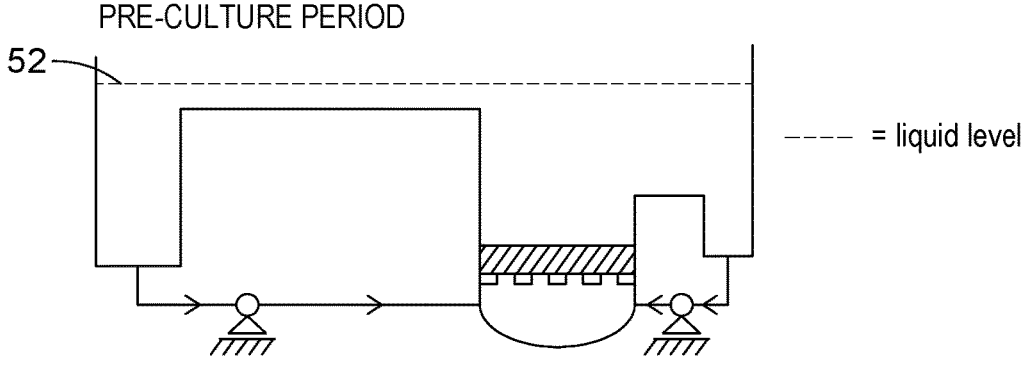
FIG. 3 shows the system of FIG. 1 indicating the first fluid fill level.
Figure 4:
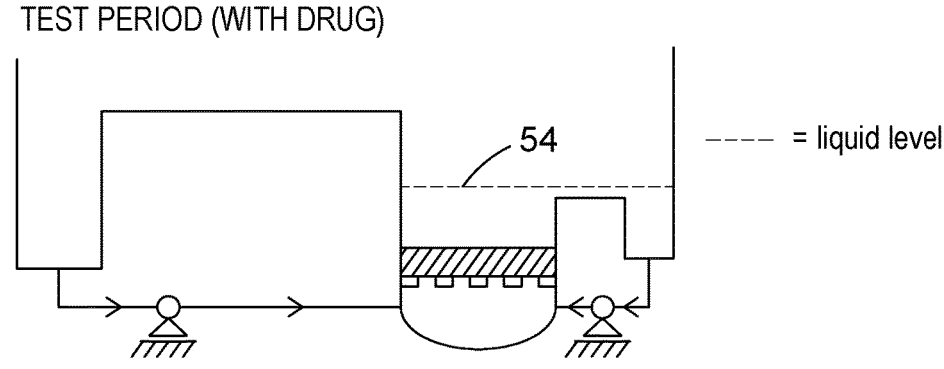
FIG. 4 shows the system of FIG. 1 indicating the second fluid fill level.

In the pre-culture period (typically 2-3 days) both the first circulation (fluid circuit 14) and the second circulation (fluid circuit 16) are filled with cell culture medium and the micropumps 32, 34 are operative (see also FIG. 3, showing the first fluid fill level). In the test period (see FIG. 4, showing the second fluid fill level), the first circulation is emptied and fresh cell culture medium containing the drug to be tested is added only to the second circulation, to the second fluid fill level 54. The micropump 34 for the second circulation is run at a rate equal to the sum of the rates for both micropumps 32, 34 in the pre-culture period. This ensures the flow conditions experienced by the cells in the scaffold do not change between the pre-culture and test periods. As the first micropump 32 is not run, it is apparent that both micropumps 32, 34 must be under independent control. Given that the volume of the second circulation is low (~200 µL), but the cell number in the scaffold high (~600 k), the test period can typically be short, for example, less than or equal to 24 hrs. The short times described will enable the use of serum and/or protein free medium which simplifies metabolic analysis as protein binding is eliminated.

After the assay is run for the desired period (typically 1-24 hours), a sample of the culture medium can be removed and analysed in an appropriate manner to determine the metabolite content. Standard techniques may be used for this; for example, liquid chromatography.

To reduce the risk of evaporation from the system, but particularly from the lower-volume second circulation, reservoirs 40, 42, 44, 46 are provided close to the second circulation which can be filled with liquid to increase the local relative humidity. This is important as evaporation of cell culture medium during the test period can lead to inaccurate concentration measurements, and consequently incorrect determination of metabolic rate. A shorter duration test is also helpful to reduce evaporation.

An additional benefit to the use of the microphysiological system as disclosed here is that non-parenchymal cell types of the liver can be included in the 3D scaffold. This allows metabolism to be assessed under a range of physiological and pathological conditions (e.g. inflammation).

Figure 5:
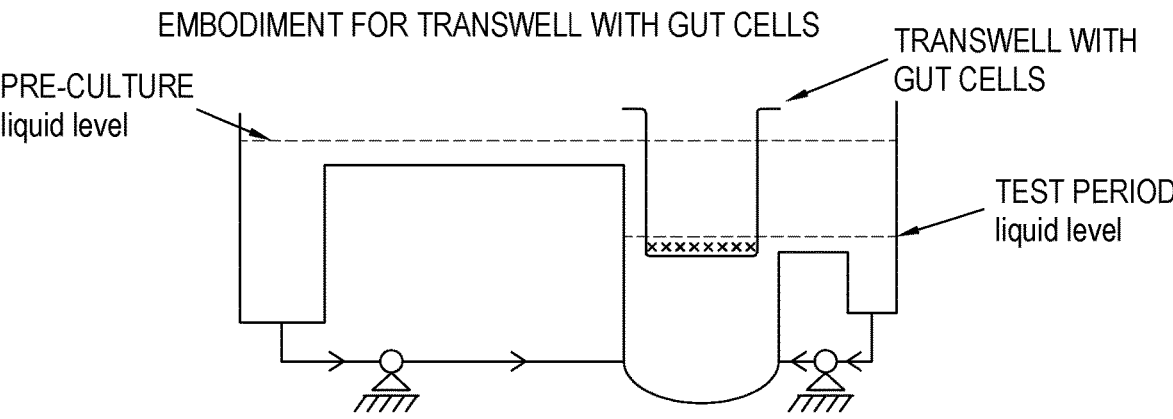
FIG. 5 shows a schematic side sectional view of a microphysiological cell culture system according to an alternative embodiment of the invention.

Further, it is not necessary to use a 3D cell scaffold, or to use liver cells. Alternative embodiments in which the cells are from organs other than the liver (e.g. lung, gut, kidney) are possible as are alternative formats for the cell culture (e.g. monolayer, transwell). FIG. 5 shows an embodiment in which a transwell insert including intestinal cells is used in place of the 3D scaffold. Other features are the same.

To compare the cell number to medium volume ratio of the described system and other competitor technologies, figures from Table 2 of Chan et al have been used:

Suspension hepatocyte assay—cells per well 50K, volume in well 50 µL—1 million cells per ml. However, the assay can not be conducted for more than 6 hrs.

Hepatopac assay—cells per well 5 k, volume in well 64 µL—0.078 million cells per ml. Assay takes at least 7 days. Assay as Described Herein:

Pre-culture period—cell per well 600 k, volume in combined circulations 2000 µL—0.3 million cells per ml. Cultured for 3 days.

Test Period—cell per well 600 k, volume in second circulation only 200 µL—3 million cells per ml. Assay for 1-24 hrs.

Thus, the present invention provides a system which allows easy switching from a pre-culture, low cell number to volume ratio system, to a test high cell number to volume ratio system. This permits rapid analysis of potentially rare or low level metabolites. For example, the 3D liver scaffold single loop system described in Vivares et al 2015 can be used to study metabolism of disopyramide and timolol. Both compounds are considered to be slowly metabolised. Whilst the single loop system is metabolically active enough to enable metabolism to be measured the test phase requires 5 days to give measurable changes. With the double loop system proposed herein, we predict that the test phase would be shortened to less than 1 day. This offers a time saving and also helps to eliminate evaporation issues which can occur in long tests without medium exchange.

Further advantages of the present invention include the maintenance of highly functional cells for many weeks. The recirculating of culture medium allows for the build-up of metabolites; many other microphysiological systems are single pass, ie the medium only contacts the cells once for a short period then leaves the system, which gives insufficient time for metabolism.

The overall length of the assay is short compared to the hepatopac system (4 days for the present system including pre-culturing, compared with at least 7 days for hepatopac, not including pre-culturing time). The use of hepatopac cultures permits extended test periods, but evaporation will be a significant issue over this length of time when using small volumes in microtitre plates. There is a long overall assay time (even ignoring the pre-culture period for hepatopac); and the hepatopac system contains both human cells and supporting murine cells, which may confound analysis of metabolism.

The system is also advantageous compared with culture of suspensions of primary human hepatocytes, which offer a reasonable approximation to the metabolism of the human liver. Importantly, the test/assay time is limited to 6 hours as cells die. Even during the 6 hour assay cell viability and hence metabolic competence declines significantly with time. It is well known that suspension hepatocytes can not be used for the assessment of slowly metabolised compounds as the compounds can not be kept in contact for sufficient time to achieve measurable metabolism. Increasing the cell to medium ratio to overcome this issue is not possible as in the wells of standard microtitre plates the limits of nutrient supply, particularly oxygenation is reached.

An alternative is provided by the relay method, which overcomes the short culture time of suspension hepatocytes. As described by Di et al, the relay is performed using 5×4 hr incubations. In each incubation 250 k cells are used (0.5 million cells per ml, 0.5 ml volume). Thus to complete 5 incubations 1.25 million cells are required. This is 2.1 times more cells than used in the assay disclosed herein, and the cell to medium ratio is lower.

The invention claimed is:

1. A microphysiological cell culture system, the system comprising:
   a cell culture chamber;
   first and second fluidic circuits, each connected to said chamber at a first and second fluidic circuit chamber outlet and a chamber inlet, wherein at least the first and second circuit chamber outlets are at separate positions;
   wherein the cell culture chamber defines a first fluid fill level and a second fluid fill level, the first fluid fill level representing a greater volume of fluid than the second fluid fill level; and
   wherein the first fluidic circuit chamber outlet is positioned at the first fluid fill level or between the first and second fluid fill levels, and the second fluidic circuit chamber outlet is positioned at or below the second fluid fill level; such that either the first or both first and second fluidic circuits are able to operate when the chamber is filled with fluid to the first fill level, and only the second fluidic circuit is able to operate when the chamber is filled with fluid to the second fill level.

2. The system of claim 1, wherein the cell culture chamber defines a location for receiving cells, said location being positioned at or below the second fluid fill level.

3. The system of claim 1, wherein the first and second fill levels are defined by walls of the cell culture chamber of first and second heights, said walls defining the first and second chamber outlets.

4. The system of claim 3, comprising a further wall enclosing both first and second walls of the cell culture chamber.

5. The system of claim 3, wherein either or both of the first and second chamber outlets are in the form of a spillway leading from and defined by the first and/or second walls.

6. The system of claim 1, wherein the first fluidic circuit has a volume which is at least 2, 3, 5, 10, 25 times greater than the volume of the second fluidic circuit.

7. The system of claim 1, wherein the first fluidic circuit is at least 10, 25, 50, 100 times longer than the second fluidic circuit.

8. The system of claim 1, wherein the first fluidic circuit comprises at least a portion which is exposed to an environment.

9. The system of claim 1, wherein the first and second fluidic circuits each comprise a micropump.

10. The system of claim 1, further comprising at least one reservoir which is not part of the fluidic circuits for receiving a liquid.

11. The system of claim 10, wherein said at least one reservoir is adjacent the second fluidic circuit.

12. The system of claim 1, wherein the chamber further comprises a cell culture.

13. The system of claim 12, wherein the cell culture is comprised within a 3D scaffold; a cell culture insert with a permeable membrane; or a flat surface with a monolayer of cells.

14. The system of claim 1, wherein at least said second fluidic circuit and cell culture chamber comprise cell culture medium.

* * * * *